(12) United States Patent
Ledley

(10) Patent No.: US 8,483,966 B1
(45) Date of Patent: Jul. 9, 2013

(54) METHOD FOR INCREASING UTILIZATION OF GENETIC TESTING

(75) Inventor: Fred David Ledley, Needham, MA (US)

(73) Assignee: National Biomedical Research Foundation, Bethesda, MD (US)

( * ) Notice: Subject to any disclaimer, the term of this patent is extended or adjusted under 35 U.S.C. 154(b) by 539 days.

(21) Appl. No.: 09/630,631

(22) Filed: Aug. 1, 2000

Related U.S. Application Data

(60) Provisional application No. 60/146,742, filed on Aug. 2, 1999.

(51) Int. Cl.
*G01N 33/48* (2006.01)
*C12Q 1/68* (2006.01)

(52) U.S. Cl.
USPC .............................................. 702/19; 435/6

(58) Field of Classification Search
USPC ............................ 702/19, 20; 395/200; 705/2
See application file for complete search history.

(56) References Cited

U.S. PATENT DOCUMENTS

| | | | | |
|---|---|---|---|---|
| 5,757,917 A | * | 5/1998 | Rose et al. | 705/79 |
| 5,876,926 A | * | 3/1999 | Beecham | 435/5 |
| 5,978,466 A | * | 11/1999 | Quattrocchi | 379/265.01 |
| 6,018,713 A | * | 1/2000 | Coli et al. | 705/2 |
| 6,055,487 A | * | 4/2000 | Margery et al. | 702/84 |
| 6,141,653 A | * | 10/2000 | Conklin et al. | 705/80 |
| 6,192,320 B1 | * | 2/2001 | Margrey et al. | 702/84 |
| 6,287,254 B1 | * | 9/2001 | Dodds | 600/300 |
| 2002/0007285 A1 | | 1/2002 | Rappaport | |
| 2004/0029138 A1 | | 2/2004 | Allan et al. | |

OTHER PUBLICATIONS

Williams-Jones, Health Law Journal (Canada), vol. 7, pp. 49-67 (1999).*
Advisory Committee on Genetic Testing, Code of Practice and Guidance on Human Genetic Testing Serivces Supplied Direct to the Public (London: Health Departments of the United Kingdom, 1997): <http://www.dh.gov.uk>.*
Tarczy-Hornoch et al. "Creation and Maintenance of Helix, a Web Based Database of Medical Genetics Laboratories, to Serve the Needs of the Genetics Community," Proc AMIA Symp (1998) pp. 1-5.*
McKinnon et al, The Familial cancer program of the Vermont Cancer Center: Development of a cancer genetics program in a rural area. Journal of Genetic Counseling, 6(2): 131-145, 1997.
Advisory Committee on Genetic Testing: Code of Practice and Guidance on Human Genetic Testing Services Supplied Directly to the Public by John Polkinghorne (Sep. 1997).
U.S. Office Action dated May 12, 2009 for U.S. Appl. No. 10/134,424.

* cited by examiner

*Primary Examiner* — Anna Skibinsky
(74) *Attorney, Agent, or Firm* — Foley & Lardner LLP

(57) ABSTRACT

This invention describes a method and site for providing genetic testing using the Internet which enables individuals to access genetic testing as well as methods that ensure privacy in the selection of genetic tests, payment, performance of tests, delivery of results, interpretation of results, and genetic counseling. These methods will increase the utilization of genetic testing by individuals.

20 Claims, 8 Drawing Sheets

Mygenome.com    Using Mygenome.com ☐
Our guarantee of privacy ☐
Click here to enter your private records
ID name [          ] Password [          ]
Become a new subscriber    ☐

The risk of stroke is due to both genetic and environmental factors such as diet. Genetic testing can help predict your risk of stroke and guide the choice of effective therapy. Our experts recommend testing for:
ApoE. Apolipoprotein E is a protein in the blood which carries fats such as cholesterol to different parts of the body. Individuals having certain forms of ApoE are at increased risk of stroke and should be treated with cholesterol lowering drugs.
    for more information on this test ☐    to order this test ☐
MTHFR. Methylenetetrahydrofolate is an enzyme in cells that regulates the level of a critical amino acid, homocysteine. Individuals having certain forms of MTHFR are at increased risk of stroke and should be treated with vitamins folate and B12 to reduce the risk of stroke.
    for more information on this test ☐    to order this test ☐
<more>
ALSO:    Genetic tests to avoid drug toxicity and drug interactions from therapy for stroke
    Genes causing hypertension or blood clotting disorders increase risk of stroke

FIG. 2

Mygenome.com  Using Mygenome.com ☐
Our guarantee of privacy ☐
Click here to enter your private records
ID name [ John Doe ] Password [ xxxxxx ]
Private sample code: [ xxxxxx ]
Click here to become new subscriber ☐

| | |
|---|---|
| Sample code: | xxxxxx |
| Collection date: | January 12, 2000 |
| Quality: | passed |
| Sample: | available |
| Tests performed to date: | BRCA-1    Report:  normal |
| | p53                normal |
| | Tay Sachs          carrier    more information ☐ |

New tests to be performed:
ApoE          Sample: available    Report time: 2 weeks    Cost: $200.00
Order this test ☐    Do not order this test ☐
Order additional tests now ☐
Process this order now ☐

When testing for ApoE, our experts recommend testing also for LPL which can also elevate cholesterol

FIG. 3

Mygenome.com  Using Mygenome.com ☐
Our guarantee of privacy ☐
Click here to enter your private records
ID name [ John Doe ] Password [ xxxxxxx ]
Private sample code: [ xxxxxxx ]
Click here to become new subscriber ☐

Sample code:            xxxxxxx
New tests to be performed:
ApoE                    Sample: available     Report time: 2 weeks    Cost: $200.00
LPL                     Sample available      Report time: 2 weeks    Cost $100.00
Method of payment:
Credit card: number [          ]              expiration date [          ]
Invoice: existing account number: [          ]
Do you need documentation of this test for third party reimbursement ☐
Open new account: ☐

Will my HMO or insurance pay for this test?
How to obtain reimbursement: ☐

FIG. 4

Mygenome.com   Using Mygenome.com
Our guarantee of privacy
Click here to enter your private records
ID name [ JohnDoe ]  Password [ xxxxxxxx ]
Private sample code: [ xxxxxxxx ]

Informed consent (Click here to review full informed consent forms):
I hereby authorize Mygenome to distribute a portion of the sample identified by [        ] and [            ] to a genetic testing laboratory selected by Mygenome for the sole purposes of studying the genes *MTHFR* and *CBT* to determine which forms of these genes are present in my cells.

I understand that I will be able to access the results of these tests through Mygenome.com only through the use of the ID name and private sample code that I have provided above together with a confidential password that I have selected. After accessing these results, I may, at my sole discretion, choose to share this information with my healthcare providers, HMO, or insurance companies. I understand that all reasonable efforts will be made by Mygenome its employees, and contractors to protect the confidentiality of these results in accordance with all applicable state and federal laws.

I understand that the results of these tests may have practical consequences for my future health care. I have been informed by Mygenome that that expert genetic counseling is recommended and is is available to help me interpret the results of these test and make decisions regarding my health care.

I hereby signify my consent to this testing by providing the ID name and private sample code given above and by entry of my electronic signature.   Proceed: [          ]
Cancel: ☐

FIG. 5

Mygenome.com   Using Mygenome.com  ☐
                   Our guarantee of privacy ☐
                   Click here to enter your private records
                   ID name [ John Doe ] Password [ xxxxxxx ]
                   Private sample code: [ xxxxxxx ]

The following tests have been ordered:
MTHFR          Report time: 2 weeks  Cost:    $200.00
CBT            Report time: 2 weeks  Cost     $100.00
                      Total:                  $300.00
                      Billed to:              acct# 120984

Results will be available from mygenome.com within two weeks. To access the results, you will need to have your ID name, password, and private sample code. Keep these numbers private to protect the confidentiality of your results.

Would you like to be notified when the test results are posted?

| email | regular mail | telephone | no notice |

FIG. 6

Mygenome.com   Using Mygenome.com   ☐
                   Our guarantee of privacy ☐

Enter your private ID name and password here
ID name [          ] Password [          ]

When you become a subscriber for the first time, mygenome will arrange with you to collect a DNA sample that will be stored with a private sample code for your privacy. This sample can be used over and over again to perform any genetic tests that you may order in the future. You will will only be asked to provide a sample once. This sample will be stored at mygenome so that it can be used each time you choose to perform a gest. Confidentiality is protected by the use of an ID name which you will be asked to provide, a password which you select, and a private sample code that will be assigned to the sample. Only you know your ID name, password and private sample code which is on the sample, only you can order tests to be performed, and only you can see the results.

To become a subscriber:

Type an ID name in the box above. This may be your name, or any other name you wish to use to identify the sample. WARNING: Only you will know the ID name associated with your account. Mygenome will only identify samples by the name you provide.

Type a password in the box above. This may be any set of 10 characters. WARNING: Please remember this password which will be required to enter the private web site, to order tests and to review the results. Only you will know this password.

FIG. 7

Mygenome.com   Using Mygenome.com ☐
Our guarantee of privacy ☐

Enter your private ID name and password here
ID name [ John Doe ] Password [ xxxxxxx ]

To submit a sample:
Mygenome will send you a kit which will allow you or any health care professional you select to submit a sample of blood or a scraping of your tissues to Mygenome. The procedure for obtaining blood is similar to that individuals with diabetes use to test their glucose every day. This involves collecting several drops of blood from a finger prick. Once the sample is submitted to Mygenome, it will be protected by the ID name you have entered above and a private sample code which will be printed on the tube. This sample can be used over and over again for tests that you want performed in the future.
Please enter the address to which the sample submission kit should be sent.
(Note:Mygenome will not associate this information with your sample or results.)
Person:
Address:
Telephone number:

Note: All communications with Mygenome are considered to be highly confidential. At mygenome, you will only be identified by the ID name you have provided.

FIG. 8

METHOD FOR INCREASING UTILIZATION OF GENETIC TESTING

CROSS REFERENCE TO RELATED APPLICATIONS

This application claims the benefit of the filing date of provisional application, U.S. Ser. No. 60/146,742 filed Aug. 2, 1999.

BACKGROUND OF THE INVENTION

In general, this invention concerns the use of the Internet or world wide web to provide genetic testing. This invention describes a site and methods which singularly or together provide genetic testing including methods for using the Internet or world wide web to provide individuals with access to genetic testing and methods that ensure privacy in the selection of genetic tests, payment, performance of tests, delivery of results, interpretation of results, and genetic counseling. These methods will increase the utilization of genetic testing by individuals.

The following information is provided to assist the understanding of the reader, none of that information is admitted to be prior art to the present invention.

The human genome project is expected to identify approximately 100,000 different genes within the human genome. The sequences of these genes and the expression of the RNA and protein encoded by these genes are critical determinants of individual development, health, and disease. Variations in the sequences of these genes and in the characteristics of the products expressed from these genes underlies many aspects of human individuality including physical and mental characteristics, growth, longevity, health, and disease.

The terms "genetic test" or "genetic testing" refer to the analysis of DNA, RNA, or protein in a sample from an individual which determines, without limitation, the sequence of one, or more than one, gene within the sample, the presence or absence of one, or more than one, genetic marker, variance, mutation, polymorphism, or microsatellite sequence associated with a gene, the presence of one, or more than one, viral sequence, viral-like sequence, or repetitive sequence, a haplotype spanning one, or more than one, gene, the number of copies of one, or more than one, gene, the amount or characteristics of RNA or protein expressed from one, or more than one, gene, the arrangement of genes within the genome, the chromosome number, or integrity of chromosomes. This invention specifically concerns genetic tests useful in medicine for diagnosing genetic disease, determining an individual's propensity to multifactorial diseases, and predicting an individual's response to therapeutic drugs. Genetic tests have been developed for many inherited diseases including, but not limited to, Huntington's Disease, Cystic Fibrosis, and Phenyketonuria. Genetic tests have also been developed for genes that predispose to diseases including, but not limited to, atherosclerosis, heart failure, stroke, anemia, cancer, clotting disorders, dementia, endocrine diseases, and pulmonary diseases. Genetic tests have also been described which predict the pharmacokinetic and pharmacodynamic characteristics of many drugs including, but not limited to, drugs for the treatment of elevated cholesterol, drugs to treat cancer, drugs to reduce hypertension, and drugs to treat dementia.

New genetic tests are being discovered at a rapid rate due to continuing progress of the human genome project and clinical research using genomic tools. Genetic tests are likely to have a dramatic impact on health and disease, enabling predisposition testing and interventions to prevent disease before morbidity is apparent, providing early diagnosis and therapy, and optimizing pharmacological interventions with drugs that are likely to be safe and effective for an individual. The discovery and development of a genetic test is commonly described in scientific and medical journals and textbooks of medicine, genetics or clinical pathology, and the existence and utility of such tests is commonly known to one skilled in the art. Many genetic tests are known in the art and are described in reference books such as Scriver et al., The Molecular Basis of Inherited Disease, McGraw Hill or McKusick's Mendelian Inheritance in Man. Many genetic tests are described on the internet at sites such as www.genetests.org or many academic, sites, commercial sites, or sites dedicated to specific disease entities by non-profit, patient support groups.

The internet or world wide web is also likely to have a dramatic impact on healthcare. The term "e-health" refers to sites on the Internet that provide medical information, products, or services to individuals or to health care providers. More than 30% of all adults, and more than 70% of Internet users, visited e-health sites on the Internet in 1999. The term "site" refers to the software and hardware accessible through a URL (Universal Record Locator) or address on the Internet or world wide web and includes, without limitation, the concept, design, construction, appearance, organization, function, and content of materials posted and accessed at that URL. Current e-health sites focus on providing medical information and the sale of drugs, materials, equipment, or other products commonly available through healthcare providers or pharmacies.

Kits which enable individuals to perform home certain diagnostic tests including tests for pregnancy, glucose (diabetes), and blood clotting times are available through e-health sites or through healthcare providers or pharmacies. Kits for HIV (AIDS) testing have also been developed.

The utilization of genetic tests and the interpretation of genetic tests is significantly more complex than conventional diagnostic testing either by healthcare providers or using kits for home testing. First, the number of potential tests arising from human genomics is very large compared to the number of conventional diagnostic tests commonly performed. The genome project is expected to reveal 10,000-100,000 genes that may be analyzed by genetic tests, and each gene may contain many different genetic variations. Second, the use of genetic tests requires interpretation of the results and genetic counseling unlike conventional testing where the results are easily interpretable by comparing the amount of a product or level of activity relative to a normal range. Finally, informed consent and genetic counseling is often required for genetic tests, and often mandated by law, to assist individuals in the use of genetic information. This invention provides methods that enable selection of an appropriate genetic test and provides for the interpretation of results and genetic counseling by an individual. The term "providing genetic testing" refers to the process of procuring a sample to be tested, selecting a genetic test or test from among the many genetic tests that are developed, and reporting rest results. Providing genetic testing may include the additional steps of interpreting test results, providing genetic counseling (when necessary), or combining genetic test results with other medical information. This invention describes a method for providing genetic testing that enables individuals to utilize genetic tests in personal healthcare and lifestyle decisions.

Despite the potentially great impact of genetic tests on health care, the utilization of genetic tests is currently very limited. It should be recognized that, to date, only a fraction of the genes in the genome have been characterized, and only a small subset of variations that are predictive of disease or its response to therapy have been described. Nevertheless, it would be advantageous to develop methods for making these tests available to individuals who may realize personal benefit from predicting, preventing, or treating disease, and that these methods would have general applicability in enhancing the utilization of genetic tests and their potential impact on medical care as the number of tests increases over the next decades.

In current practice, genetic testing is controlled by health care providers such as physicians, practitioners specialized in genetics such as M.D., Ph.D., or M.A. trained geneticists or genetic counselors, and practitioners specializing in the care of individuals with disabilities or inherited genetic diseases. Genetic testing generally requires a referral from a health care provider. Samples are generally obtained by the health care provider or a central blood drawing service of a hospital or health care clinic, and samples are commonly sent to genetic testing services, often referred to as reference laboratories, such as Genzyme Genetics (genzyme.com), Quest Diagnostics (questdiagnostic.com), Gene Screen (genescreen.com), or others for testing. Genetic tests are also performed in hospital or academic laboratories. The selection of a genetic test is generally accessible only by health care providers and is generally not accessible to individuals. The present invention provides a method and enabling capabilities that are not anticipated by current practice in which health care providers have the central role in the process of selecting genetic tests, receiving the results, interpreting the results, and genetic counseling.

The methods described in this invention enable genetic testing to be controlled by the individual. These methods empower the individual without referrals to health care providers by providing the individual with access to genetic testing via the Internet or world wide web. These methods replace the need to obtain samples through a hospital or health care clinical with the ability of individuals to provide samples on their own. These methods provide individuals with access to the information required to select tests and the ability to select tests performed by genetic testing services or reference laboratories and provide for the results of these tests to be reported directly to the individual. These methods also provide the individual with the information required to interpret the tests and information for genetic counseling. Most important, the methods that are described will provide a high degree of privacy and minimize the risk of compromising the confidentiality of the individual, their decision to seek genetic testing, and the results.

Information concerning the availability of genetic testing and its utilization is commonly advertised only to health care providers and is generally not accessible to individuals. In addition, the results of genetic tests are commonly reported directly to the health care provider providing the referral. The interpretation of a genetic test is generally performed by a health care provider who has specialized training in genetics and is trained in how to interpret the results of a genetic test and provide genetic counseling. Patient support groups specializing in certain disorders or classes of disorders are often an important source of information concerning the interpretation of test results. These organizations generally do not provide testing directly, but require that individuals work through health care providers. The present invention provides a method that is not anticipated by the use of the Internet of world wide web by these organizations which provide information about specific diseases. The present invention provides integration of a diverse set of services required to select genetic tests to interpret the results, provide genetic counseling, store and distribute samples for genetic tests, and pay for tests while providing protection for individual privacy.

One of the major limitations of current practice is that it provides little privacy to individuals who may be concerned that the results of the genetic test could be used to a discriminate against them and provides many risks to confidentiality due to the number of different people and services that are involved. Every interaction with a different health care provider and every medical record that contains information on genetic tests and the results of genetic tests is a potential risk to the individual's privacy. Integrating the services necessary for genetic testing, and providing these services directly to the individual, reduces these risks and will increase the utilization of genetic testing.

There are Several Reasons that Genetic Testing Remains Underutilized:

Limited Individual Demand for Genetic Tests.

Information about genetic testing and its applications to improve medical care is complex and not widely available to individuals. Many health care providers have little background in genetics and are not able to provide individuals with information on tests that may be available and how they may benefit individual care. The ability to select genetic tests for individuals is generally restricted to a limited number of health care professionals who have the sufficient information to make such selection.

Certain genetic tests which identify an untreatable condition are often considered to have little clinical utility in the opinion of a health care provider and are often not offered to individuals. Nevertheless, many individuals are interested in having such genetic tests, even if they do not lead to therapy, simply to know whether they do, or do not, have a risk factor for a particular disease. This may lead to changes in lifestyle that may have a positive impact on the individual, their quality of life, their ability to utilize supportive resources, and their families. Information on the utility of genetic tests which enables individuals to select tests that are in their interest will increase utilization of genetic tests.

Concern about Privacy and Discrimination.

There is profound concern about the potential misuse of genetic information to discriminate against individuals who may have specific genetic variances. There is particular concern that individuals with specific genes or variant forms of genes may be discriminated in terms of access to health care, the cost of health care, employment, insurance (life, disability, health, etc.), and in social interactions. The legacy of eugenics, persistent racism, and popular perceptions concerning genetic and ethnic differences among individuals heightens concern that genetic information about individuals will be used for discrimination. There is an extensive literature on the importance of maintaining the privacy and confidentiality of genetic records to prevent such abuse, and laws designed to ensure the privacy of genetic records and prohibit discrimination are now widespread. Nevertheless, individual concern that the results of genetic tests may be misused by health care providers, insurers, employers, or even the government continues to limit the utilization of many genetic tests. Concern about privacy and discrimination is probably the single most important factor limiting the utilization of genetic tests today.

Poor Access Through Health Care Providers.

Health care providers frequently have little experience with genetic testing and many clinical laboratories may be unfamiliar with the procedures for procuring a genetic test and properly processing samples such that a test can be performed. This lack of information and experience represents a further barrier to making genetic testing widely available to individuals.

Segmented Testing Capabilities Among Many Different Genetic Testing Services or Reference Laboratories.

Genetic testing is provided by a limited number of genetic testing service providers. Many genetic tests are proprietary, meaning that one or more genetic testing services have a license which allows them to perform certain tests, while other genetic testing services are prohibited from performing such tests. As a result, it is sometimes necessary to obtain multiple samples and send the different samples to different genetic testing services to perform a complete series of genetic tests. This added complexity represents another significant barrier to making genetic testing widely available to individuals.

Inadequate Genetic Knowledge to Interpret the Results of Genetic Tests and Provide Counseling.

Genetic counseling is a critical element of genetic testing. Few health care providers or individuals have sufficient knowledge to interpret the results of a genetic test and perform genetic counseling. The need for genetic counseling in conjunction with genetic testing is mandated by law in certain jurisdictions. The inability of many health care providers to provide such counseling is another impediment to the widespread use of genetic testing, limiting the likelihood both that a physician will recommend a test and that the individual will realize the potential benefits from the test.

Public Policy.

Public policy regarding genetic testing is guided by the dual goals of using genomic information as a means for improving health and the treatment of disease, and real concern about the potential abuses of genetic information. Laws have been enacted in many jurisdictions to protect individuals against such abuses. These laws variously set standards for protecting the confidentiality of genetic records, set limits on the use of genetic information, and require genetic counseling to be provided in conjunction with genetic testing. In some cases, the added complexity of compliance, and potential penalties for noncompliance, with laws governing the privacy of medical records containing genetic information is a further impediment to the utilization of genetic testing.

Recognizing that it would be Advantageous to Improve the Utilization of Genetic Testing, the Inventor has Developed Methods which Address the Limitations Listed Above. These Methods Include:

Offer Tests with Information about their Clinical Utility to Individuals.

A method for increasing utilization of genetic testing is to make information concerning tests and their clinical utility directly available to individuals.

Direct Marketing to Individuals Through World Wide Web.

A method for increasing utilization of genetic testing is to market genetic tests directly to individuals by the Internet and world wide web. With individuals increasingly turning to the Internet for information on medical care and medical services, a web site that directly provides individuals with high quality information about genetic tests and the ability to select tests directly without the intermediation of health care providers or referrals from health care providers will increase the utilization of genetic testing.

Ensure Privacy of all Tests and Results.

A method for increasing utilization of genetic testing is to eliminate or minimize the need for intermediation by health care providers and provide individuals with direct access to genetic tests. Specifically, the method enables all aspects of genetic testing including the provision of information about the availability and utility of tests, selection of a test, procurement of samples for testing, processing of the test sample, payment for the test, and reporting of test results, interpretation of the test results, and counseling to be provided through direct and private communications with the individuals via the Internet. This method also includes strategies for collecting, storing, and distributing samples for genetic tests that protect patient privacy. Elements of this method include two, or more than two, of the following: (i) collecting a sample directly from individuals that can be used for one, or more than one, genetic test; (ii) encoding the samples with a private code and sending samples to genetic testing services for testing identified only by this code; (iii) enabling individuals to access information concerning genetic tests and select genetic tests through a web site protected by a password or private code; (iv) enabling individuals to pay directly for genetic tests without involvement of healthcare providers, managed care organizations, or third party payers; (v) providing the results of genetic tests directly to individuals ensuring privacy through the use of a password or private code; (vi) providing individuals with sufficient information to interpret the results of the genetic test and for genetic counseling through a web site protected with a password or private code. Methods for private communications via the Internet, world wide web, or alternate media including without limitation mail, fax, interactive television, or telephone, including financial transactions and the transmission of confidential information are known in the art.

An important aspect of this method is that privacy is significantly enhanced by eliminating or minimizing the role of health care providers, third-party payers, and others in procuring samples, ordering tests, payment, interpretation of results, reporting of results, genetic counseling, and reimbursement. It may be recognized that individuals may choose to make genetic information available to health care providers or may choose to accept reimbursement from third-party payers for the cost of such tests, and that such choices may limit the privacy provided by the methods described in this invention.

Provide Individuals with Direct Access to Information Required to Select Tests.

A method is described for providing individuals with access to high quality information about genetic tests, the ability to select genetic tests, direct reporting of test results, information required to interpret the test results, information for genetic counseling, and referrals for genetic counseling without the intermediary role of the health care provider. This method is an important departure from current methods for providing information to individuals and procuring genetic tests which currently requires intermediation by one or more health care providers.

Provide Storage of Samples and Sample Distribution for Testing.

A method for increasing the utilization of genetic testing is to provide a resource for storing samples that can be used for a series of genetic tests selected by the individual over time and distributing aliquots of this sample to genetic testing providers when tests are selected by the individual. Samples are preferably collected directly by the individual or may be collected by a health care provider at the direction of the individual. Samples can be collected by a variety of methods known in the art and may include blood, tissue scrapings, hair, or bodily fluids or secretions. It will be recognized that samples for genetic testing can be stable for many years and can be used repeatedly as a source of materials for genetic tests. The method involves establishing central facilities for storing samples identified only by a private code. When a test is ordered by an individual providing a password or private code that matches the sample, an aliquot of the stored sample is distributed to the appropriate genetic testing service identified only by a private code for genetic testing. Many aliquots can be taken from a single sample, and aliquots can be sent to several different genetic testing services which offer different proprietary tests or perform multiple tests at different times without the need for the individual to provide multiple samples.

One of the simple but important benefits of this invention is that by storing samples for genetic tests, it will be possible to perform multiple tests over a period of months to years without the need to obtain additional samples. This is possible because the fundamental genetic material of the individual does not change significantly over time. It will be recognized that the need to obtain a sample, by, for example, having blood drawn, is unpleasant and, in itself, an impediment to genetic testing. Thus, the storage of a sample that may be used for genetic testing makes it easier for an individual to choose to utilize genetic testing.

It is recognized that the Internet and world wide web are recognized as a means for ordering many different products and services and disseminating information about companies and their products. Many genetic testing services currently maintain sites on the world wide web which describe the company's business and the services they provide. Some provide information of a general nature of links to other sites with genetic information. The present invention provides a method that is not anticipated by these established uses of the Internet and world wide web, namely the integration of two, or more than two, of the following steps in genetic testing including selection, reporting of results, interpretation and counseling together with the storage of samples for genetic tests, mechanisms to procure tests from various providers and distribute samples for testing, and mechanisms to protect individual privacy.

Provide source of high quality information. The method involves the provision of high quality information to aid the selection of tests as well as the interpretation of the results of genetic tests and genetic counseling. The method involves creation of a set of information which can be accessed by individuals via the world wide web or other media. This information may comprise, but is not limited to, text in books, pamphlets or electronic format, video, audio, or interactive computer systems. This information can be ordered by individuals through the Internet using a password protected web site to preserve confidentiality. This method will provide superior genetic counseling to that available from many health care providers and satisfy mandated requirements for providing such counseling. This will also allow individuals to access information at an appropriate level of complexity and detail without involving additional health care providers or payers that represent a risk to privacy. Most important, the quality of this information can be controlled in a way that is not possible when counseling is provided by a health care provider who may not have in depth training in either genetics or the process of genetic counseling.

It is also recognized that a great deal of information about genetic disease, the genetic causes of disease, and genetics in general is available via Internet and the world wide web. Much of this information is provided by sources that are not qualified to assist individuals in the selection of genetic tests, interpretation of the results of genetic tests or genetic counseling. In some cases, information available on the Internet and world wide web is not designed to provide quality genetic care, but rather further political, scientific, or religious goals. In many cases there is misinformation available on the Internet and world wide web. In other cases, the information on the Internet or world wide web is of high quality and highly technical (for example Genbank, on-line medical and scientific publications, Medline, genetests.org) and is intended for use by professional scientists or health care providers, and is not suitable for use by many individuals. The present invention provides a service that is not anticipated by these established uses of the Internet and world wide web by providing high quality information designed explicitly to be useful to an individual in the selection of genetic tests, interpretation of the results, and genetic counseling.

New Testing Paradigm for Social Acceptance.

This method meets the dual societal goals of making the benefits of genetic information available to individuals to improve health care while providing protection against the use of this information for discrimination. This method is also designed to meet social and legal mandates for confidentiality and privacy of genetic information and genetic counseling. This method dramatically changes the focus of genetic testing from current methods and those known in the art which require health care providers to serve as intermediaries in genetic testing. Eliminating the need for intermediation by health care providers by providing the individual with the information and access necessary to select genetic tests and receive and interpret the results represents a fundamentally new method for utilizing genetic testing. By providing the individual with control over genetic testing and a maximum degree of privacy, societal concerns are addressed to a level far greater than current practice.

Other features and advantages of the invention will be apparent from the following description of the preferred embodiments and from the claims.

BRIEF SUMMARY OF THE INVENTION

This invention describes a method for providing genetic testing comprising two, or more than two, of the steps of:
  collecting and storing a sample;
  posting a list of genetic tests and information concerning genetic test;
  selecting of a genetic test or tests from said list;
  distributing an aliquot of said sample to a genetic testing service to perform said genetic test or tests; and
  posting the results of said tests in a manner that may be accessed by an individual.
  posting materials for interpreting the results of said test that may be accessed by said individual;
  posting materials for genetic counseling that may be accessed by said individual;
  posting a program to aid the individual in the selection of genetic tests, interpreting the results of said test, or genetic counseling that may be accessed by an individual.

In a preferred embodiment of this method, the selecting of a genetic test or tests is performed by an individual. In a preferred embodiment of this method, the collection of a sample is performed by an individual.

In a preferred embodiment of the invention, two, or more than two, steps are enabled in an integrated manner. In a preferred embodiment of the invention, two or more than two steps are enabled in an integrated manner through a site accessible via the Internet. In alternative embodiments of the invention the method comprises more than seven, more than five, or more than three steps performed in an integrated manner.

An object of this invention is a site which provides genetic testing to an individual by enabling two, or more than two, of the steps of:

collecting and storing a sample;
posting a list of genetic tests and information concerning genetic tests;
selecting of a genetic test or tests from said list;
distributing an aliquot of said sample to a genetic testing service to perform said genetic test or tests
posting the results of said tests in a manner that may be accessed by said individual;
posting materials for interpreting the results of said test that may be accessed by said individual; and
posting materials for genetic counseling that may be accessed by said individual.
posting a program to aid the individual in the selection of genetic tests, interpreting the results of said test, or genetic counseling that may be accessed by said individual.

A preferred object of the invention is a site which enables the selecting of a genetic test or tests by an individual. A preferred object of the invention is a site which enables the collecting of a sample by an individual.

A specific objection of the invention is a site which enables two, or more than two, steps to be performed in an integrated manner. An alternative objects of the invention is a site that enables more than seven, more than five, or more than three of the steps enumerated above to be performed in an integrated manner.

The preferred embodiment of this invention is a method of providing genetic testing in which an individual makes the selection of a genetic test or tests comprising one, or more than one, of the steps of:
collecting and storing a sample;
posting a list of genetic tests and information concerning genetic tests that may be accessed by an individual;
distributing an aliquot of said sample to a genetic testing service to perform said genetic test or tests; and
posting the results of said tests in a manner that may be accessed by said individual.
posting materials for interpreting the results of said test that may be accessed by said individual;
posting materials for genetic counseling that may be accessed by said individual;
posting a program to aid the individual in the selection of genetic tests, interpreting the results of said test, or genetic counseling that may be accessed by said individual.

In alternative embodiments of this method, three, five, or seven of the steps enumerated above are provided in an integrated manner. In a preferred embodiment of this method, three five, or seven of the steps enumerated above are provided in an integrated manner though a site accessible through the Internet. The preferred method is one in which collection of a sample is performed by said individual.

BRIEF SUMMARY OF THE DRAWINGS

FIG. 2. The site enables individuals to receive information about specific genetic tests and order these tests using an integrated system.

FIG. 3. The site enables individuals to review the results of genetic tests performed previously in a private genetic medial record and can select tests that they would like to have performed FIG. 4. The site enables individuals to pay for genetic tests that they have selected using a credit card or other confidential financial instrument. The site also directs individuals how to obtain reimbursement from third party payers.

FIG. 5. The site provides individuals with information about genetic test sufficient to provide informed consent and enables individuals to provide a legally binding informed consent.

FIG. 6. The site enables individuals to order tests online and receive results in an integrated manner. In this example, individuals are asked to indicate how they would like to be notified when the results are available.

FIGS. 7 and 8. The site enables individuals to submit a sample for DNA banking. This sample will be identified only by a private code and can be used for genetic testing over a period of many years.

DETAILED DESCRIPTION

Figure 1:
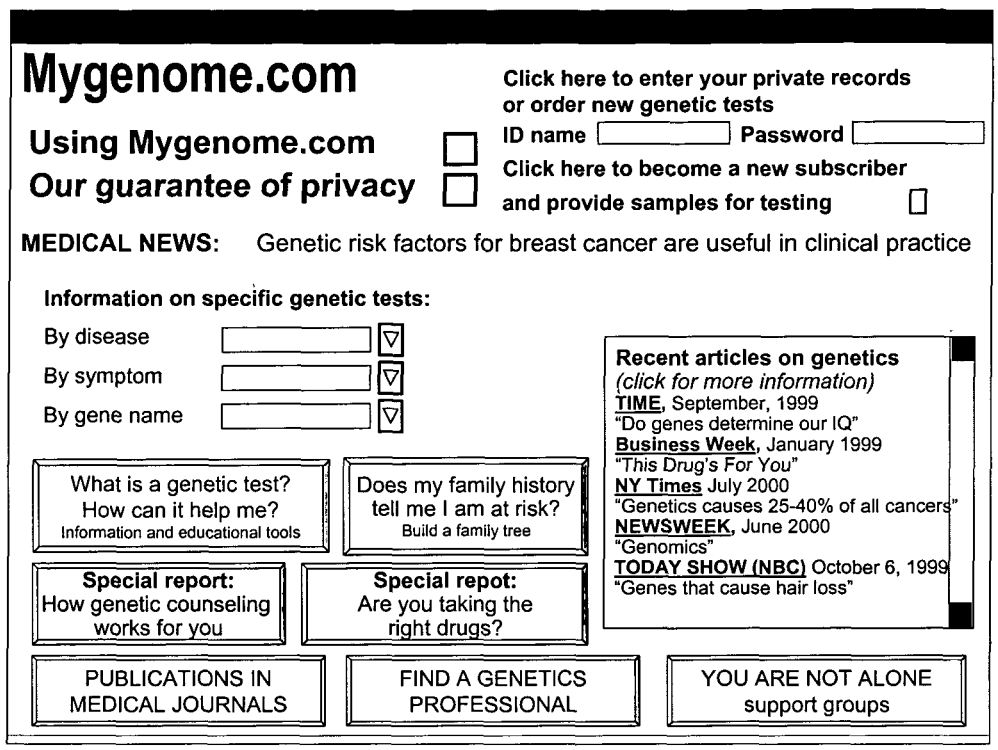
FIG. 1. A model of a site described in this invention. The site contains a posting a list of genetic tests and information concerning genetic tests that may be accessed by an individual, a mechanism which enables individuals to select and pay for genetic test, a posting of results of genetic tests performed for the individual, and a posting of materials for interpreting the results of genetic tests. This home page demonstrates the integration of information about genetic tests, test results, information for counseling with mechanisms for individuals to access this information, select tests, and receive results and counseling at the site.

This invention concerns the use of the Internet or world wide web to provide genetic testing and methods for providing such services to individuals. The term "providing genetic testing" refers to the process of procuring a sample to be tested, selecting a genetic test or test from among the many genetic tests that are developed, and reporting rest results. Providing genetic testing may include the additional steps of interpreting test results, providing genetic counseling (when necessary), or combining genetic test results with other medical information.

This invention describes a method for utilization of genetic testing comprising the steps of:
collection and storage of a sample;
posting a list of genetic tests and information concerning said tests that may be accessed by an individual;
selection of specific genetic tests by an individual;
distributing an aliquot of the said sample to a genetic testing service to perform said tests;
posting the results of said tests that may be accessed by an individual;
posting materials for interpreting the results of said test and genetic counseling that may be accessed by an individual.

This invention describes a site which enables individuals to utilize genetic testing through the steps of:
collection and storage of a sample provided by an individual;
posting a list of genetic tests and information concerning said tests that may be accessed by an individual;
selection of specific genetic tests by an individual;
distributing an aliquot of the said sample to a genetic testing service to perform said tests;
posting the results of said tests that may be accessed by an individual;
posting materials for interpreting the results of said test and genetic counseling that may be accessed by an individual.

An alternative embodiment of the invention is a method for utilization of genetic testing involving the selection of genetic tests by an individual and one, or more than one, of the following steps:

collection and storage of a sample provided by an individual;

posting a list of genetic tests and information concerning said tests that may be accessed by an individual;

distributing an aliquot of the said sample to a genetic testing service to perform said tests;

posting the results of said tests that may be accessed by an individual;

posting materials for interpreting the results of said test and genetic counseling that may be accessed by an individual;

posting a program to aid the individual in the selection of genetic tests, interpreting the results of said test, or genetic counseling that may be accessed by an individual.

An alternative object of this invention is a site enabling the selection of genetic tests by an individual and one, or more than one, of the following steps:

collection and storage of a sample provided by an individual;

posting a list of genetic tests and information concerning said tests that may be accessed by an individual;

distributing an aliquot of the said sample to a genetic testing service to perform said tests;

posting the results of said tests that may be accessed by an individual;

posting materials for interpreting the results of said test and genetic counseling that may be accessed by an individual;

posting a program to aid the individual in the selection of genetic tests, interpreting the results of said test, or genetic counseling that may be accessed by an individual.

An alternative embodiment of the invention is a method for utilization of genetic testing involving the collection and storage of a sample provided by an individual and one, or more than one, of the following steps:

posting a list of genetic tests and information concerning said tests that may be accessed by an individual;

selection of specific genetic tests by an individual, distributing an aliquot of the said sample to a genetic testing service to perform said tests, posting the results of said tests that may be accessed by an individual posting materials for interpreting the results of said test and genetic counseling that may be accessed by an individual.

posting a program to aid the individual in the selection of genetic tests, interpreting the results of said test, or genetic counseling that may be accessed by an individual.

An alternative object of the invention is a site which enables the collection and storage of a sample provided by an individual and one, or more than one, of the following steps:

posting a list of genetic tests and information concerning said tests that may be accessed by an individual;

selection of specific genetic tests by an individual, distributing an aliquot of the said sample to a genetic testing service to perform said tests, posting the results of said tests that may be accessed by an individual posting materials for interpreting the results of said test and genetic counseling that may be accessed by an individual.

posting a program to aid the individual in the selection of genetic tests, interpreting the results of said test, or genetic counseling that may be accessed by an individual.

In a specific embodiment of the invention, two or more than two, of the steps of posting, accessing, selecting, interpreting, and counseling are performed in an integrated manner via the Internet or world wide web and are integrated with the steps of collecting, distributing, and storage. The term "integrated" means available through a linked system or systems. In the preferred embodiment of this invention these steps are integrated on a site accessible via the Internet or world wide web. In an alternative embodiment of this invention these steps are integrated by alternate media including without limitation mail, fax, interactive television, telephone, or publication.

A specific object of the invention is a site which enables individuals with two or more than two, of the steps of posting, accessing, selecting, interpreting, and counseling in an integrated manner. In an alternative object of this invention the site is integrated with one, or more than one, step provided by alternate media including, without limitation, mail, fax, interactive television, telephone, or publication.

Specific embodiments of the invention involve the selection of genetic tests by an individual and two, or more than two, of the steps of posting, accessing, interpreting, and counseling are provided in an integrated manner via the Internet or world wide web and are integrated with the steps of collecting, distributing, and storage. A specific object of the invention is a site which enables for selection of genetic tests by an individual and two, or more than two, of the steps of posting, accessing, interpreting, and counseling. In an alternative object of this invention the site is integrated with alternate media including without limitation mail, fax, interactive television, telephone, or publication.

An object of this invention is a site on the Internet or world wide web containing a posting of genetic tests that may be selected by an individual. A specific object of this invention is a site on the Internet or world wide web for selection of tests by an individual which provides for two, or more than two, of the steps of collecting, distributing, storage, posting, accessing, interpreting, and counseling in an integrated manner. In an alternative embodiment of this invention one, or more than one of the steps of collecting, distributing, storage, posting, accessing, interpreting, or counseling are provided for by alternate media including without limitation mail, fax, interactive television, telephone, or publication.

An object of this invention is a site on the Internet or world wide web which enables individuals to access information about genetic tests, select genetic tests, access the results of said tests, and access information required to interpret the results of said tests or access information required for genetic counseling. In specific embodiments, the site on the Internet or world wide web enables the individual to access one, two, or more than two of the following: (i) information about genetic tests, (ii) selection of genetic tests, (iii) the results of said tests, (iv) information required to interpret the results of said tests, or (v) information required for genetic counseling. In a specific embodiment, access to the site, or portions of the site, requires a password or private code. In an alternative embodiment, the site is integrated with alternate media including without limitation mail, fax, interactive television, telephone, or publication which provide one, or more than one, of these functions.

An embodiment of this invention is the collection and storage of samples provided by an individual for the purposes of distributing aliquots of samples to genetic testing services to perform tests selected by an individual. A specific embodiment of this invention is the distribution of aliquots of samples to genetic testing services to perform tests selected by an individual.

An object of this invention is a site which enables individuals to access and select genetic tests, the results of genetic tests, the interpretation of the results or genetic counseling which utilizes passwords and private codes to ensure the privacy of the individual. A further object of this invention is a site which utilizes passwords and private codes to ensure the privacy of an individual accessing and selecting genetic tests, the results of the genetic tests, the interpretation of the results, or genetic counseling. A further object of this invention is a site that uses private codes to ensure the privacy of samples collected, stored or distributed for genetic tests. In a specific object of this invention, the samples which are distributed to genetic testing services contain a private code and not the name of the individual.

The terms "Internet" or "world wide web" are known in the art and refer to electronic networks, or elements of electronic networks, for the exchange of information between individuals and includes, without limitation, public systems such as the world wide web and public or private systems providing access to sites on said network including, without limitation, companies with private networks accessed by telephone, cable, wireless devises, or satellite or sites providing portals for entry into any public or private network. The term "site" refers to the software and hardware accessible through a URL (Universal Record Locator) or address on the Internet or world wide web and includes, without limitation, the concept, design, construction, appearance, organization, function, and content of materials posted and accessed at that URL.

Methods for constructing and operating the site anticipated by this invention including the software to create and operate the site and the hardware and Internet connections that make sites available over the Internet are generally known in the art, are described in many books for lay and professional users of the Internet, and are available from commercial vendors. For example, FrontPage (Microsoft Corporation) is a simple computer program which can be used to create a site. More sophisticated sites are generally created directly in languages such as HTML and Java by companies dedicated to webdesign and construction. Sites are commonly linked to various databases. For this invention, the site may be linked to databases of information about genetic testing, a database of individuals who use the site, and databases containing personal genetic or medical records. Databases may be constructed and maintained using commercially available software such as Oracle. Digital signatures can be used implemented using VeriSign Secure Digital ID. Payment may be made by credit card or by way of Cyber\Cash. A payment system may also include software for correctly calculating sales tax and specifying shipping options such as Taxware and TanData. A site is commonly hosted on a server by an ISP (Internet Service Provider) such as UUNet, Genuity, ATT or Verio. The site anticipated by this invention could be hosted on a commercially available server such as a Compaq Enterprise Hosting NT system and run Microsoft Site Server Edition 3.0 and SQL Server Database. Various security systems and systems for encrypting data are known in the art and are generally available in major browser products. These systems are used to protect the privacy of individual medical and financial records that may be available through the Internet. While this invention will benefit from continuing advances in Internet software, hardware, and practices, the elements required to construct and operate the site anticipated by this invention are generally available in the art.

A specific object of this invention is a site that integrates two, or more than two, steps required to provide genetic testing services as enumerated above. Specific objects of this invention are the software and hardware capable of carrying out the unique methods and embodiments described including without limitation, the concept, design, construction, appearance, organization, function, and content of a site that integrate the multiple steps required to provide genetic services. Specific embodiments also include the software and hardware capable of carrying out the unique methods and embodiments described including without limitation, the concept, design, construction, appearance, organization, function, and content of a site integrated with alternate media including without limitation mail, fax, interactive television, or telephone to provide genetic testing.

The term "individual" refers to, without limitation, any person including a patient as well as family, friends, or agents of a person or patient other than those working in their capacity as health care providers. The term "individual" excludes biopharmaceutical companies and their agents or affiliates and the organizers, sponsors, staff, or investigators of clinical trials. The term "health care provider" is commonly known in the art and includes, without limitation, physicians, practitioners specialized in genetics such as M.D. or Ph.D. trained geneticists or genetic counselors, practitioners specializing in the care of individuals with disabilities or inherited genetic diseases.

An embodiment of this invention is the collection and storage of samples provided by an individual. The terms "collection" or "collecting" refer to the process of obtaining a sample from an individual that contains DNA in a form that can be used for genetic testing. In a preferred embodiment of this invention, collection is performed by the individual and the sample is then sent to a central facility for storage. The terms "storage" or "storing" refer to the process of maintaining the samples under conditions that preserve the integrity of the sample such that it can be used for genetic testing together with a system for tracking the location of the sample so that it can be retrieved. In a preferred embodiment, the samples are stored and used for multiple genetic tests to be performed at different times. A "central facility" is a facility that has the equipment and resources necessary to preserve and track the sample in an integrated manner with posting. A central facility may be operated in accordance with FDA or CLIA (Clinical Laboratory Improvement Amendments) regulations. In alternative embodiments of this invention the sample may be collected by an individual or a health care provider and sent to the central facility. In the preferred embodiment of this invention the sample is collected by the individual.

An embodiment of this invention is the storage of the sample in a central facility identified with a private code such that aliquots of the sample can be distributed to genetic testing providers. The term "private code" refers to a series of alphanumeric characters which provide a unique identifier for each sample. In an alternative embodiment of this invention the private code could be a fingerprint, handwriting sample, electronic voice print, or other unique identifier of the individual known in the art.

The term "sample" refers to, but is not limited to, an aliquot of blood, hair, cells from a scraping of skin, mucosal membranes, or other body part, or bodily secretion including saliva, mucous, urine, or feces useful for genetic testing. The term sample also refers to, without limitation, DNA, RNA, protein or other materials useful for genetic testing extracted or purified from sources such as an aliquot of blood, hair, cells from a scraping of skin, mucosal membranes, or other body part, or bodily secretion, for example saliva, mucous, urine, or feces.

In specific embodiments of this invention the sample is collected in a container or on an absorbent surface. A "container" is a device that holds the sample. Various containers for holding samples are known in the art. The container commonly comprises a surface or contains reagents that prevent degradation of the sample as well as a closure mechanism that protects the sample from the environment. Various containers are known in the art. An "absorbent surface" commonly comprises a sheet of material which can hold or bind the sample. Various absorbent surfaces for holding or binding samples are known in the art. In specific embodiments the absorbent surface can be used to purify DNA, RNA or protein. In a preferred embodiment of this invention, the container or absorbent surface allows a sample to be collected by an individual. Specific objects of this invention are the containers that enable individuals to collect samples.

In a specific embodiment of this invention the sample is collected in stored such that the sample can be separated into aliquots that can be sent to different genetic testing services. The term "aliquot" refers to an amount of the sample, a container or absorbent surface containing a sample, or DNA, RNA, or protein purified from a sample in an amount sufficient to perform a genetic test and in a form suitable for performing said tests.

In a preferred embodiment of this invention the sample is collected by the individual using a puncture device to draw blood which is placed in a container or on an absorbent surface. In a specific embodiment the device is designed specifically to causes a puncture of the skin sufficient to collect the amount of blood required for testing. In specific embodiments the puncture is sufficient to collect more than one drop. In preferred embodiments, the puncture is sufficient to collect 5-10 drops or 200-500 ul of blood. In a further embodiment, the device contains both elements designed to puncture the skin and a container or an absorbent surface designed to store the sample. In an alternative embodiment of this invention, the sample is collected by the individual as hair or by scraping of skin, mucosal membranes or other body part or bodily secretion including, but not limited to, saliva, sputum, or feces.

In a specific embodiment of this invention the individual is provided with a container or absorbent surface with a private code and this code is used to store and label the sample. In a specific embodiment the container or absorbent surface is labeled with a fingerprint, handwriting sample, electronic voice print, or other unique identifier of the individual known in the art. In an alternative embodiment the container or absorbent surface is labeled by the individual using a private code. In specific embodiments the container or absorbent surface is labeled with a print, type, array of spots or marks, a magnetic strip, bar code, or other media for automatic reading. In a specific embodiment, the container or absorbent surface does not contain the name of the individual. A specific object of this invention is a container or absorbent surface which is labeled with a private code, fingerprint, handwriting sample, electronic voice print, print, type, array of spots or marks, magnetic strip, bar code or other unique identifier of the individual known in the art and does not contain the name of the individual.

An object of this invention is a site which includes the posting of information for access by individuals which may be used to select tests, interpret results or for genetic counseling. The term "posting" or "posted" refers to making a source of information available for access by individuals. The terms "accessing" or "access" refers to the ability of an individual to retrieve, receive, or review the information that is posted. In specific embodiments of this invention there is posted two, or more than two, of the following elements: (i) a list of available genetic tests; (ii) information that enables an individual who accesses this list to select tests that may be of interest to them, (iii) the results of genetic tests, (iv) information for the interpretation of genetic tests, (v) information for genetic counseling concerning genetic test results, (vi) programs to assist the individual with selecting a genetic test, interpreting test results, or genetic counseling. In a specific embodiment of this invention, the information to be posted is incorporated in a database and posting is on a site on the Internet that can be accessed via the world wide web. In a further embodiment of this invention at least one of these elements is posted on a site and one, or more than one, of these elements are posted by an alternate media including without limitation mail, fax, interactive television, telephone, or publication. In specific embodiments posting may comprise, but is not limited to, one, or more than one, of the following: alphanumeric text, pictures, pictographs, symbols, audio, voice, video, or animation.

A specific object of the invention is a site for posting. In specific embodiments the site contains two, or more than two of the following elements (i) a list of available genetic tests; (ii) information that enables an individual who accesses this list to select tests that may be of interest to them, (iii) the results of genetic tests, (iv) information for the interpretation of genetic tests, or (v) information for genetic counseling concerning the use of genetic test results, (vi) programs to assist the individual with selecting a genetic test, interpreting test results, or genetic counseling. An alternative object of the invention is a site on the Internet for posting which contains at least one of these elements integrated with the posting of one, or more than one, of these elements by an alternate media including without limitation mail, fax, interactive television, telephone, or publication.

In a specific embodiment of this invention is a posting of two, or more than two, different genetic tests that may be selected by an individual. An alternative embodiment of this invention is the posting of more than five different genetic tests that may be selected by an individual. A further embodiment of this invention is the posting of more than ten different genetic tests that may be selected by an individual. A further embodiment of this invention is the posting of more than twenty-five different genetic tests that may be selected by an individual. A preferred embodiment is the posting of more than one hundred genetic tests that may be selected by an individual. In specific embodiments there is posted on a site which enables the selection of genetic tests by an individual, information on more than two genetic tests for access by individuals which may be used to select tests, interpret results or for genetic counseling. In alternative embodiments there is posted information on more than five genetic tests, alternatively information on more than ten genetic tests, alternatively information on more than twenty-five genetic tests, or most preferably information on more than one hundred genetic tests. A specific object of this invention is a site with the posting of information on more than two, five, ten, twenty-five, or preferably more than one hundred genetic tests. An additional object of this invention is a site which enables individuals to select from more than two, five, ten, twenty-five, or preferably more than one hundred genetic tests.

In a specific embodiment of this invention accessing or access is limited to individuals having a password or private code. The term "password" refers to a set of alphanumeric characters known by the individual which allows access to the posted materials. The term password may also refer to fingerprints, handwriting samples, electronic voice prints, images, or other unique identifier of the individual known in the art. Methods for limiting access to individuals with passwords are known in the art.

"Selection" or "selecting" refers to the ordering or purchasing a genetic test to be performed on an individual sample. Selection causes a test to be performed and, in specific embodiments of this invention, causes an aliquot of a sample to be sent to a genetic testing service and the results to be provided to the individual. Selection can be made using a site and methods known in the art such as "point and click" where an icon or link on the site enables individuals to select a test. The term selection also includes payment provided to cover the cost of the test and any ancillary services.

The terms "utilization" or "utilize" refer to one or more of the selection of a genetic test, accessing the results of genetic tests, the interpretation of genetic test results, or counseling concerning genetic test results. Genetic counseling is designed to guide an individual in the utilization of genetic test results. A test may be utilized by an individual or a health care provider. Genetic tests can be utilized for many purposes including making health care choices including choices about reproduction as well as many lifestyle decisions related to diet, employment, work habits, recreational habits, retirement, education or insurance. It will be apparent that an individual who receives information about genetic tests, selects a genetic test, receives the result of a genetic test, or receives information for interpretation and counseling utilizes genetic tests, whether or not that individual chooses to make changes in their healthcare or lifestyle as a result. It will also be recognized that an individual who communicates the information about a genetic test, genetic test results, or information for interpretation and counseling to a healthcare provider also utilizes genetic tests in seeking to improve their healthcare.

An object of this invention is a site that enables the selection of genetic tests by an individual. An embodiment of this invention is the selection of genetic tests by an individual. In preferred embodiments, the test is selected by an individual who is a patient, and individual who is a family member of a patient, an individual who is a friend or agent of a patient other than those who may be working in their capacity as health care providers. In a preferred embodiment, selection is performed by an individual using a password or private code. In a further embodiment of this invention, selection is performed using information concerning the utility of a list of available genetic tests posted for access by an individual and integrated with the method for selection. In a specific embodiment of this invention the selection is made by the individual, not by a health care provider on behalf of an individual person or patient.

In specific objects of this invention, the site contains information concerning the utility of a list of available genetic tests posted for access by an individual and integrated with the method for selection.

In an alternative embodiment of this invention, the selection is made by a health care provider acting as an agent for the individual and the individual access the results of the test and information useful in selecting test, interpreting results, or genetic counseling. A specific object of this invention is a site which enables a health care provider to select genetic tests and the individual to access test results and information useful in the selection of genetic tests, the interpretation of genetic tests.

In an alternative embodiment of this invention, the selection is made by an individual with the authorization of a health care provider and the individual access the results of the test and information useful in selecting test, interpreting results, or genetic counseling. A specific object of this invention is a site which enables a health care provider to authorize an individual to select genetic tests genetic tests and the individual to access test results and information useful in the selection of genetic tests, the interpretation of genetic tests. The terms "authorize" or "authorization" refer to the action of a health care provider which enables an individual to select a genetic test. In states where a prescription is necessary for genetic testing, a health care provider may provide an authorization for individual to select tests.

In a specific embodiment of this invention, the individual provides payment as part of the process of selection by providing for use of a credit card, debit card, account, bank account, or other forms of electronic payment using methods known in the art. In an alternative embodiment of this invention, the individual provides information which allows for reimbursement from payers including, but not limited to, health insurance providers, medicare, or medicaid. In a specific embodiment of this invention, payment, forms of electronic payment, or reimbursement are arranged over the Internet or world wide web. In an alternative embodiment of this invention there is posted for access by an individual using a password or private code, information sufficient for the individual to obtain reimbursement. In an alternative embodiment of this invention, payment, use of forms of electronic payment, reimbursement, or information sufficient for reimbursement are provided by alternate media including without limitation mail, fax, interactive television, or telephone. A specific object of this invention is a site which enables individuals to pay for genetic tests by providing for use of a credit card, debit card, account, bank account, or other forms of electronic payment using methods known in the art. In an alternative object of this invention, is a site which enables individuals to access information which allows for reimbursement of genetic tests from payers including, but not limited to, health insurance providers, medicare, or medicaid.

In a further embodiment of the invention the process of selection involves providing informed consent. By "informed consent" is meant a process by which individuals receive information about a genetic test that they may wish to select, and provide legally binding consent for such a test to be performed on their sample. Consent may be given using electronic signatures or other legal methods known in the art including without limitation mail or fax. In a further embodiment of this invention the informed consent may include a program or a self-assessment test in which individuals are presented with questions to assess their knowledge about a test that they wish to select. A specific object of this invention is a site that enables individuals to give informed consent for a genetic test.

An object of this invention is a site that controls the distribution of an aliquot of a sample to genetic testing service to perform a test selected by an individual. An embodiment of this invention is the distribution of an aliquot of a sample to a genetic testing service to perform the test selected by an individual. The term "distribution" refers to sending an aliquot of a sample from a central facility where the sample is stored to a genetic testing service for the purposes of performing a selected genetic test. In an embodiment of this invention the sample is distributed to a genetic testing service that is not associated with the central facility for DNA storage. In an alternative embodiment, the sample is distributed to a genetic testing service that is associated with the central facility for DNA storage. A specific object of this invention is a site which enables individuals to track the progress of a sample within a central facility through distribution to a genetic testing service.

An embodiment of this invention is that the selection of a genetic test by an individual, payment, or reimbursement are integrated with the distribution of an aliquot of the sample, or DNA purified from the sample, is distributed to a genetic testing service that is capable and qualified to perform the selected test. The tests selected by the individual are then performed by the genetic testing service. The term "associated" refers to genetic testing services that have the same ownership as the central facility, are majority owned by the central facility, own a majority of the central facility, share majority personnel with the central facility, share working facilities with the central facility. Associated does not refer to genetic testing services that have contracts to perform work for the central facility. The term "genetic testing service" refers to any entity capable and qualified to perform selected genetic tests and includes, without limitation, specialized genetic testing services, diagnostic reference laboratories providing genetic testing, hospital laboratories, clinical chemistry laboratories, or other entities performing genetic testing. Genetic testing services may be regulated by federal agencies including the FDA or CLIA.

The terms "genetic test" or "genetic testing" refer to the analysis of DNA, RNA, or protein in a sample from an individual which determines, without limitation, the sequence of one, or more than one, genes within the sample, the presence or absence of a genetic marker, variance, mutation, polymorphism, or micro satellite sequence associated with a gene, the presence of a viral sequence, viral-like sequence, or repetitive sequence, a haplotype spanning one, or more than one, gene, the number of copies of one, or more than one gene, the amount or characteristics of RNA or protein expressed from a gene, the arrangement of genes within the genome, the chromosome number, or integrity of chromosomes. This invention preferably concerns genetic tests useful in diagnosing genetic disease, determining an individual's propensity to multifactorial diseases, and predicting an individual's response to therapeutic drugs. Excluded from the definition of genetic tests are tests to determine paternity or maternity or for forensic analysis, or to determine sex, even if such tests incorporate elements of genetic analysis, since such tests are generally not useful for medical purposes.

The term "gene" is commonly known in the art and is a linear sequence of nucleotides within the human genome that encodes a biological function. A gene commonly directs the expression of RNA or protein which may be directly responsible for carrying out the function encoded by the gene, or the RNA or protein may be modified to carry out such functions. The gene may include introns, exons, promoters, or other sequences which are involved in directing the biological function. It is recognized to those in the art that the sequence of nucleotides (a,g,c,t) within the gene which encode its function may vary in different individuals, and that variances or mutations within the sequences of nucleotides may change the function. A "variance" or "mutation" is a specific sequence within a gene that is an identifies genes with specific functions or contributes to specific functions. A "genetic marker", "polymorphism", "single nucleotide polymorphism" (SNP), or "micro satellite sequence" are specific sequences within a gene that identify genes with specific functions, though such sequences often do not contribute to that function. Those skilled in the art will recognize that the terms variance, mutation, genetic marker, polymorphism, SNP are often used interchangeably.

A genetic test is distinct from paternity or maternity testing or forensic testing, even if such tests involve the analysis of DNA or protein from an individual. Such tests are not useful in diagnosing genetic disease, determining an individual's propensity to multifactorial diseases, and predicting an individual's response to therapeutic drugs. Moreover, such testing does not involve specific genes or genetic marker, variance, mutation, polymorphism, or micro satellite sequence associated with a gene, but commonly involve anonymous markers throughout the genome.

A preferred embodiment of this invention is that the aliquot of the sample that is distributed is identified only by a private code. In alternative embodiments, the sample may contain a private code together with other identifying information.

An embodiment of this invention is the posting of the results of the genetic test for access by the individual. A specific embodiment of this invention is the posting of results of the genetic test for access by individuals through a password or private code. The term "results" refers to the determination, using a genetic test, of the sequence of a gene or the presence or absence of one, or more than one, genetic markers, variance, mutation, polymorphism, or micro satellite sequences associated with a gene, the presence of a viral sequence, viral-like sequence, repetitive sequence, a haplotype spanning one, or more than one, gene, the number of copies of one, or more than one, gene, the amount or characteristics of RNA or protein expressed from a gene, the arrangement of genes within the genome or information concerning the chromosome number or integrity of chromosomes, all being the subject of genetic tests known in the art. In an alternative embodiment of this invention, the results are posted for access by health care providers. A specific object of this invention is a site for posting the results of genetic tests for access by an individual.

An object of this invention is a site with the posting of materials for interpreting the results of said test and material and genetic counseling that may be accessed by an individual using a password or private code. "Interpreting" the results means relating the technical description of the test result, namely the sequence of one, or more than one, gene within the sample, the presence or absence of a genetic marker, variance, mutation, polymorphism, or micro satellite sequence associated with a gene, the presence of a viral sequence, viral-like sequence, repetitive sequence, a haplotype spanning one, or more than one, gene, the number of copies of one, or more than one, gene, the amount or characteristics of RNA or protein expressed from a gene, the arrangement of genes within the genome or information concerning the chromosome number or integrity of chromosomes to a specific medical condition or risk of a specific medical condition. Examples of interpretation include, but are not limited to, the determination of whether a specific change in the nucleotide sequence is normal or likely to cause disease or determining whether a haplotype corresponds to a form of a gene with a predictable genetic effect.

"Counseling" means providing information concerning the use of the results of a genetic test in choosing medical care, assessing disease risk, family planning, or personal activities. Examples of counseling include, but are not limited to, determining the likelihood that an individual will have a certain form of cancer based on the results of a genetic test, determining the likelihood of an inherited certain genetic disorder based on the results of a genetic test, or selecting a drug which is likely to be safe and effective based on the results of a genetic test. An embodiment of this invention is the posting of information concerning genetic tests, for selection, interpretation, or counseling. A further embodiment is a site which can be accessed by an individual that integrates selection, interpretation, or counseling. A preferred embodiment is the access to such information or site using a password or private code. In alternative embodiments, the posting of such information are provided by alternate media including without limitation mail, fax, interactive television, telephone, or publication. In an alternative embodiment there is posted a list of genetic counselors or health care providers with expertise or geographical proximity required to provide counseling to the individual.

An object of this invention is a site that provides individuals with access to materials for use in interpreting or counseling including, but not limited to, text in books, pamphlets or electronic format, video or audio, or interactive computer systems or other interactive media, such material being posted on the Internet or world wide web or provided via an alternate media including, but not limited to, mail, fax, interactive television, telephone, or publication. An alternative object of this invention is a site with posted information for the individual identifying health care providers who specialize in interpreting or genetic counseling. In a specific embodiment of this invention, there is posted a catalogue of materials for interpreting or counseling that may be purchased by accessing the posted information using a password or private code.

In further embodiments of this invention, one, or more than one, non-genetic tests are performed in conjunction with the genetic test which are useful in selecting, interpreting or counseling. Non-genetic tests may include, but are not limited to, blood tests to determine the content of cells, proteins, salts, enzymes, carbohydrates, fats, or other constituents of the blood, or tests performed on urine or feces. In a preferred embodiment, the individual can access information, select such tests, and access the results through a system integrated with genetic testing.

An object of this invention is a program for collecting information concerning an individual useful in the selection of a genetic test, interpretation of a genetic test, or genetic counseling where said program is posted on the Internet or world wide web and is accessed using a password or private code. A specific embodiment of this invention is a program useful in the selection, interpretation, or counseling where said program is posted on the Internet or world wide web and is accessed using a password or private code. The term "program" means an interactive medium such as a questionnaire or a computer program which is accessed via the world wide web which involves queries for information concerning the individual where such information is useful in selection, interpretation, or counseling. In alternative embodiments, the program is posted by an alternate media including, but not limited to, mail, fax, interactive television, telephone, or publication. A program may consist of software, hardware, or printed materials and may involve one, or more than one of, a database with an individual's medical records, statistical or analytical analysis, or links to clinical databases or published medial information. A specific object of the invention is the posting of a program on the site. An alternative object of the invention is the posting of a program comprised of software by mail.

An object of this invention is a site with the posting of a program for collection of information about the individual including, but not limited to, their health, development, medical history as well as their genetic or family history, their medical history, as well as a genetic or family history which would be useful in selecting, interpreting, or counseling. In a specific embodiment this posting can be accessed only with a password or private code. In a specific embodiment, there is posted a program which uses the collected information to assist the individual in selecting a genetic test. In a specific embodiment there is posted a program which uses the collect information to assist the individual in selecting, interpreting, or counseling. In alternative embodiments, the program is posted by an alternate media including, but not limited to, mail, fax, interactive television, telephone, or publication.

An embodiment of this invention is the posting of an individual record which can be accessed through the Internet or world wide web using a password or private code where the information in the record is useful in the selection of genetic tests, interpretation of test results, or genetic counseling. The term "record" means a compilation of information about the individual such as a medical record including, but not limited to, the results of genetic tests, the results of non-genetic tests, a history of health, development, and illness, or a genetic or family history. In a specific embodiment of this invention, the individual record is compiled using a program. In alternative embodiments of this invention, the individual record is provided by the individual or health care providers. In alternative embodiments, the record is posted by an alternate media including, but not limited to, mail, fax, interactive television, telephone, or publication.

The invention is illustrated further by the following examples, which are not to be taken as limiting in any way. It should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

EXAMPLE 1

Genetic Testing for Prevention of Breast Cancer

An individual concerned about her risk for breast cancer accesses information about genetic tests which predict the risk of cancer through a site such as mygenome.com. The site contains information about tests for genes including BRCA1, BRCA2, p53, p21, p16 and other genes that have been implicated as predisposing factors for breast cancer. The individual selects a password which provides private access to additional information at the site and enables her to select genetic tests which she would like performed. The site also contains a program which queries the individual about her family history or breast cancer, age of menstruation, age of first pregnancy, and exposure to potential carcinogens, all of which have been implicated as risk factors for breast cancer.

Because of her family history or breast cancer, the patient, guided by a program on the site, selects to have a test for mutations in the BRCA1 gene. The individual also chooses to provide a sample herself. Through the site, the patient requests that an appropriate container be sent to her which enables her to provide a sample of blood from a finger prick (equivalent to a glucose stick). The container is pre-labeled with a private code. Using the appropriate device and container, several drops of blood are obtained and the sample is returned to the central facility. The individual retains the private code number of her sample.

Using the password the individual accesses mygenome.com, selects the BRCA1 test, and provides the private code that identifies her sample. She also chooses to pay by a credit card, rather than involve third party payers, and provides the account information for a VISA card. She also asks for documentation that will allow her to seek reimbursement at a later date.

Once the test is selected, the central facility removes an aliquot of the sample and, with the sample identified only with the patient code, sends the aliquot to Myriad Diagnostics, Inc. which has proprietary tests for mutations in BRCA1. The results of the test are provided to mygenome.com and are posted for the patient by confidential mail and on mygenome.com such that it can only be accesses with her password.

Two variances in the sequence of the BRCA1 gene in the individual are identified by the genetic test that are different from the "normal" consensus sequence. To interpret the results, the individual accesses mygenome.com using her password and learns that one of the variances that was identified is common in people of her ethnic origin and is thought to have no effect on the risk of breast cancer. The other variance has been reported in individuals with a moderate risk of breast cancer if there are also mutations in a second gene BRCA2. The individual therefore selects to have an additional test performed for BRCA2, chooses again to pay using her VISA card, and another aliquot of the sample is then sent for BRCA2 testing identified only by a private code. The results show that there are no mutations in the BRCA2 gene.

The individual seeks counseling information through mygenome.com using her password and accesses information which indicates that she may have a risk of breast cancer 1.5-2 times that of individuals who have no mutations in BRCA1. She also learns that there is an ongoing study of the use of Tamoxifen to prevent breast cancer in individuals with mutations in BRCA1. She is provided with the name and address of a local health care provider who is expert in the prevention and treatment of breast cancer as well as the name and address of an investigator performing this trial. She chooses to contact the investigator of this study and, through the site, asks that the results of the BRCA1 and BRCA2 tests be sent to this investigator.

This example illustrates that the accessing, selecting, testing, interpreting and counseling for genetic testing is performed in a fully confidential and private manner using private communications through the Internet and through the storage and distribution of samples identified only by private codes. Using this method, the individual is able to access quality information required to select genetic tests that may have an important impact on her future health without risking a loss of privacy and attendant discrimination.

EXAMPLE 2

Genetic Tests Predicting Common Diseases

Most common diseases are caused by a combination of genetic and environmental factors. Such diseases occur at higher frequency in individuals who have mutations in one or more critical genes, but also require the coincidence of environmental factors. Genetic testing for such diseases can be effective in identifying whether an individual is at risk so that the environmental factors which contribute to the disease can be avoided or treated through changes in lifestyle or healthcare. Examples of genetic tests that predict the risk of common disorders are:

| Disorder | Genetic test |
|---|---|
| Cancer | Breast Cancer (BRCA1)*; BRCA1; Ovarian Cancer (BRCA1) |
|  | Breast Cancer (BRCA2)*; BRCA2; Ovarian Cancer (BRCA2) |
|  | p53 |
|  | p21 |
|  | p16 |
|  | Ataxia Telangectasia |
|  | Familial Colorectal Cancer; Familial Colon Cancer |
|  | Medullary Thyroid Carcinoma; MTC |
|  | Others . . . |
| Alzheimer's Disease | Apolipoprotein E |
|  | β amyloid precursor protein |
|  | protein τ |
|  | presenilin-1, presenilin-2 |
|  | α 2-macroglobulin |
|  | a 1-antichymotrypsin |
| Heart attack, stroke | Apolipoprotein E |
|  | Lipoprotein lipase |
|  | LDL receptor |
|  | MTHFR |
| ALS | Superoxide Dismutase (SOD) |
| COPD | α 1-antitrypsin (AAT) |
| Anemia | hemoglobin S |
|  | hemoglobin C |
|  | thalassemia (α) |
|  | thalassemia (β) |
|  | G-6 PD |
| Liver failure | Hemochromatosis |
| Spina Bifida | MTHFR |

EXAMPLE 3

Genetic Tests Predictive of Drug Response

Variations in genes that affect the metabolism of drugs can increase drug levels, drug toxicity and drug interactions. Genetic tests can be used to avoid drugs that have a higher probability of toxicity and individualize the dose to maximize the therapeutic benefit while minimizing toxicity. The following are examples of tests that can be used to guide the safety and appropriate application of important drugs.

| | |
|---|---|
| CYP1A1 | Chlorinated benzenes (environmental toxin) |
| CYP1A2 | Caffeine, phenacetin, warfarin, Erythromycin, Ropivacaine, Haloperidol, antipyrine, theophylline, Paracetamol |
| CYP2C8 | TCA, Diazepam, Hexabarbitone |
| CYP2C9/10 | Phenytoin, S-warfarin, Diclofenac, Tolbutamide |
| CYP2C19 | Mephenytoin, Diazepam (Valium), TCA |
| CYP2D6 | Debrisoquine, Codeine, Dextrometorphan, b-blockers, SSRIs, others |
| CYP2E1 | Paracetamol, Isoflurane, Sevoflurane, Methoxyflurane, Enflurane, Trichorethylene |
| CYP3A4 | Nifedipine, Dextrometorphan, Alfentanil, Sufentanil, Fentanyl, Erythromycin, Lignocaine, Ropivacaine, Midazolam, Codeine, Granisetron, Hydrocortisone |
| CYP3A5 | Caffeine, Diltiazem |
| CYP3A7 | Midazolam |
| CYP17 | Pregnolone |
| CYP19 | Testosterone |
| CYP21A2 | 17-hydroxyprogesterone |

Variations in genes that affect drug targets and drug response may affect the safety and efficacy of a drug. Genetic tests can be used to avoid drugs that have a higher probability of toxicity and individualize the dose to maximize the therapeutic benefit while minimizing toxicity.

| | |
|---|---|
| Factor V | Oral contraceptives |
| Prothrombin | Oral contraceptives |
| TPMT (thiopurine methyltransferase) | Azothioprine, mercaptopurine (purine analogues) |
| 5' lipoxegenase | Zilutin (5' lipoxegenase inhibitors) |
| CETP (cholesterol ester transfer protein) | Pravastatin, others (statins) |
| ApoE (apolipoprotein E) | Tacrine (cholinesterase inhibitors, muscarinic agonists, others) |
| G-6 PD (glucose 6 phosphase dehydrogenase) | sulfur drugs |
| pseudocholinesterase | pseudocholinesterase inhibitors |
| β-receptor | Isoproterenol (β-agonists) |
| Serotonin transporter | SSRI antidepressants (Prozac, Pindolol, others) |
| acetyltransferase | isoniazid, others |
| ADH(2h) (aldehyde dehydrogenase) | alcohol |
| ACE (angiotensin converting enzyme) | Enalpril, others |
| opioid receptors | Endorphins, morphine |

EXAMPLE 4

Genetic Tests for Inherited (Single Gene) Disease

A large number or inherited genetic diseases are caused by well-characterized mutations in genes that impair the function of a gene or cause a gene to have dominant, adverse effects. Many of these tests are performed in academic, hospital clinical laboratories or in the research laboratories of scientists who study these disorders. The following is partial list of genetic tests for inherited genetic diseases. This list was derived, in part, from the site: genetests.org.

Achondroplasia*
Adenosine Monophosphate Deaminase 1*; AMPD1; Exercise-Induced Myopathy
Adrenoleukodystrophy, X-linked*; Addison Disease and Cerebral Sclerosis;
Adrenomyeloneuropathy; Adrenoleukodystrophy, Recessive*; Neonatal Adrenoleukodystrophy
Alpha Thalassemia
Alpha-1-Antitrypsin Deficiency
Amyloidosis Type I*; Amyloid Polyneuropathy, Andrade or Portugese Type; Amyloidosis, Portugese Type
Amyloidosis, Swedish Type
Angelman Syndrome
Azoospermia*; Oligospermia (CFTR)
Bloom Syndrome*
Canavan Disease
Carnitine Palmitoyltransferase Deficiency*; CPT I Deficiency; CPT II Deficiency
Carnitine Deficiency, Systemic*
Charcot-Marie-Tooth Disease, X-linked*; CMTX; HMSN, X-linked; Hereditary Motor and Sensory Neuropathy, Charcot-Marie-Tooth Disease,
Citrullinemia*
Congenital Bilateral Absence of the Vas Deferens*; CBAVD
Congenital Adrenal Hyperplasia*; 21-Hydroxylase Deficiency; CAH
Cystic Fibrosis*; CF
Cytochrome C Oxidase Deficiency*; COX Deficiency
Dentatorubral-Pallidoluysian Atrophy*; DRPLA
Duchenne Muscular Dystrophy*; BMD, included; Becker Muscular Dystrophy, included; DMD
  Dystonia Type I*; Torsion Dystonia 1, Dominant
Early Onset Familial Alzheimer Disease*; AD1; AD3; AD4; Alzheimer Disease, Type 1; Alzheimer Disease, Type
Factor V Leiden Mutation*; Resistance to Activated Protein C; Thrombophilia V (Protein C Resistance); Thrombosis Risk Factor (Factor V Leiden)
Fragile X Syndrome*; FRAXA; Martin-Bell syndrome
Friedreich Ataxia
Galactosemia*; Galactose-1-Phosphate Uridyltransferase Deficiency
Gaucher Disease*; Glucocerebrosidase Deficiency
Genotypic Gender Assignment*; XX/XY Gender Assignment
Glycogen Storage Disease Type III*; Cori Disease; Debrancher Deficiency; Forbe Disease
Glycogen Storage Disease Type VII*; PFK Deficiency; Phosphofructokinase Deficiency; Tarui Disease
Glycogen Storage Disease Type IV*; Brancher Deficiency
Glycogen Storage Disease Type V*; McArdle Syndrome
Glycogen Storage Disease Type II*; Pompe Disease
Hemochromatosis
Hemoglobin E*
Hemoglobin C*; SC Disease; Sickle Cell Disease (Hemoglobin C)
Hemoglobin S*; Sickle Cell Anemia; Sickle Cell Disease (Hemoglobin S)
Hemophilia A*; Factor VIII Deficiency
Hemophilia B*; Christmas Disease; Factor IX Deficiency
Hereditary Motor and Sensory Neuropathy, Dominant (Type 1)
Hereditary Neuropathy with Liability to Pressure Palsies*; HNPP
Huntington Disease*; HD
Hydrocephalus, X-linked*; Aqueductal Stenosis,
Hypochondroplasia
Kennedy Disease*; SBMA; Spinal and Bulbar Muscular Atrophy
Lactate Dehydrogenase Deficiency*; LDH Deficiency
Late Onset Familial Alzheimer Disease*; AD2; AD5; Alzheimer Disease (Apolipoprotein E); Alzheimer Disease, Medium Chain Acyl-CoA Dehydrogenase Medullary Thyroid Carcinoma*;
MTC
Leber Hereditary Optic Neuropathy
Marfan Syndrome*
Medium Chain Acyl-CoA Dehydrogenase Deficiency*; MCAD Deficiency
Mitochondrial Myopathy*; Kearns-Sayre Syndrome; LHON; Leigh Disease; MELAS; MERRF;
NARP
MTHFR Thermolabile Variant*; Cardiovascular Risk Factor, Neural Tube Defect Risk Factor,
Preeclampsia Risk Factor, Thrombosis Risk Factor
Multiple Endocrine Neoplasia Type 2B/3*; MEN2B; MEN3
Multiple Endocrine Neoplasia Type 2A*; MEN2A
Myotonic Dystrophy*; Steinert Disease
Neurofibromatosis Type II*; NF2
Neurofibromatosis Type I*; NF1; Von Recklinghausen Disease
Niemann-Pick Disease*
Norrie Disease*
Parentage Testing*; Maternity Testing; Paternity Testing
Phenylketonuria, Phenylalanine Hydroxylase Deficiency
Phosphoglycerate Mutase Deficiency*; PGAM Deficiency
Phosphoglycerate Kinase Deficiency*; PGK Deficiency
Phosphorylase Kinase Deficiency of Liver and Muscle*
Prader-Willi Syndrome
Protein C; Thrombophilia V (Protein C Resistance); Thrombosis Risk Factor (Factor V Leiden)

Refsum Syndrome, Adult*; Phytanic Acid Oxidase Deficiency, Adult
Refsum Syndrome, Infantile*; Phytanic Acid Oxidase Deficiency, Infantile
Rh C Genotyping
Rh D Genotyping
Rh E Genotyping
Sex-Determining Region Y*; SRY
Siemerling-Creutzfeldt Disease
Spinal Muscular Atrophy Types I/II/III*; Kugelberg-Welander; SMA; Werdnig-Hoffmann Disease
Spinocerebellar Ataxia Type VIP; Olivopontocerebellar Atrophy III; SCA7
Spinocerebellar Ataxia Type VI*; SCA6
Spinocerebellar Ataxia Type I*; Olivopontocerebellar Atrophy I; SCA1
Spinocerebellar Ataxia Type II*; Olivopontocerebellar Atrophy, Holguin; SCA2
Spinocerebellar Ataxia Type III*; Machado-Joseph Disease; SCA3
Spinocerebellar Ataxia Type VIII*; SCA8
Tay-Sachs Disease*; GM2 Gangliosidosis
Thanatophoric Dysplasia Type I*
Thanatophoric Dysplasia Type II*; Cloverleaf Skull with Thanatophoric Dysplasia;
Thanatophoric Dysplasia with Kleeblattschaedel
Thrombosis Risk Factor (Factor V Leiden)
Williams Syndrome
X Inactivation Studies
Y Chromosome Detection/Molecular Genetics
Zellweger syndrome*; Cerebrohepatorenal Syndrome
Zygosity Testing*; Twinning

EXAMPLE 5

Site for Increasing Utilization of Genetic Testing

This invention describes a site which enables individuals to select genetic test which includes a posting of genetic tests and information concerning said tests that may be accessed by an individual, enables selection of specific genetic tests by an individual including methods of payment, provides for the collection of samples from an individual and the distribution of an aliquot of the sample, the posting of the results of the test in a private medical record, the posting of materials for interpreting the results of a test and for genetic counseling that may be accessed by an individual, and the posting of programs to aid the individual in the selection of genetic tests, interpreting test results, and genetic counseling that. An important feature of the site is that the posting of information for accessing, selecting, interpreting, and counseling and mechanisms for selecting, accessing, and paying are available in an integrated manner with the steps of collecting, distributing, and storage or samples at a site on the interne. Elements of a site with these features are illustrated in FIGS. 1-7.

What I claim is:

1. A method of providing genetic testing services to an individual comprising posting
   (i) a list of genetic tests which can be run on a biological sample from said individual;
   (ii) first information concerning each of said genetic tests on said list;
   (iii) a mechanism for said individual to directly select at least one of said genetic tests by private communication over the internet without intermediation of a healthcare provider, wherein the genetic test selected by said individual is performed on a biological sample and a result of said selected genetic test is obtained;
   (iv) the result of said selected genetic test;
   (v) second information to assist in interpreting said result of said selected genetic test; and
   (vi) third information to provide genetic counseling relating to the result of said selected genetic test;
   wherein said individual has direct access to each of said first information, second information, and third information without the intermediation of a health care professional; and
   wherein said individual is a non-healthcare professional.

2. The method of claim 1 wherein said posting is on an internet address.

3. The method of claim 1 wherein said mechanism for selecting includes a mechanism for payment for said genetic test.

4. The method of claim 1 wherein said result is accessible by said individual.

5. The method of claim 2 wherein said internet address is protected by a password.

6. The method of claim 3 wherein said mechanism for selecting includes a mechanism for said individual to provide informed consent for said genetic test.

7. The method of claim 1 wherein said list of genetic tests comprises one or more types of genetic tests selected from the group consisting of genetic tests for diagnosing a genetic disease, genetic tests determinative of multifactorial disease propensity, and genetic tests predictive of a therapeutic drug response.

8. The method of claim 2 wherein said mechanism for selecting is accessible and performable by said individual.

9. The method of claim 8 wherein, said mechanism for selecting includes a mechanism for payment for said genetic test.

10. The method of claim 9 further comprising the step of posting on said internet address a result of said genetic test selected.

11. The method of claim 10 wherein said result is accessible by said individual.

12. The method of claim 11 wherein said internet address is protected by a password.

13. The method of claim 8 wherein said mechanism for selecting includes a mechanism for said individual to provide informed consent for said genetic test.

14. The method of claim 2 wherein said list of genetic tests comprises one or more types of genetic tests selected from the group consisting of genetic tests for diagnosing a genetic disease, genetic tests determinative of multifactorial disease propensity, and genetic tests predicative of a therapeutic drug response.

15. A method of providing genetic testing services to an individual comprising posting on a password protected interne address in an integrated manner
    (i) a list of genetic tests which can be run on a biological sample from said individual;
    (ii) first information concerning each of said genetic tests on said list;
    (iii) a mechanism for said individual to directly select at least one of said genetic tests by private communication over the internet without intermediation of a healthcare provider, wherein the genetic test selected by said individual is performed on a biological sample and a result of said selected genetic test is obtained, said mechanism accessible and performable by said individual, and said mechanism including a means for payment for said genetic tests and a mechanism for said individual to provide informed consent for said genetic test;

(iv) the result of said selected genetic test, said result being accessible by said individual;

(v) second information to assist in interpreting the result of said selected genetic test; and (vi) third information to provide genetic counseling relating to the result of said selected genetic test;

wherein said individual has direct access to each of said first information, second information, and third information and said result of said selected genetic test without the intermediation of a health care professional; and wherein said individual is a non-healthcare professional.

16. The method of claim 15 wherein said list of genetic tests comprises one or more types of genetic tests selected from the group consisting of genetic tests for diagnosing a genetic disease, genetic tests determinative of multifactorial disease propensity, and genetic tests predictive of a therapeutic drug response.

17. The method of claim 1 wherein said posting is accessible through a URL (Universal Record Locator).

18. The method of claim 1 wherein said posting comprises private communication over the internet.

19. The method of claim 18 wherein said private communication over the internet comprises email.

20. The method of claim 1 wherein said method is provided on an internet address and said result is also provided by email.

* * * * *

UNITED STATES PATENT AND TRADEMARK OFFICE
CERTIFICATE OF CORRECTION

| | | |
|---|---|---|
| PATENT NO. | : 8,483,966 B1 | Page 1 of 1 |
| APPLICATION NO. | : 09/630631 | |
| DATED | : July 9, 2013 | |
| INVENTOR(S) | : Ledley | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 287 days.

Signed and Sealed this
Tenth Day of February, 2015

Michelle K. Lee
*Deputy Director of the United States Patent and Trademark Office*